(12) United States Patent
Ben-Porath et al.

(10) Patent No.: US 7,217,579 B2
(45) Date of Patent: May 15, 2007

(54) VOLTAGE CONTRAST TEST STRUCTURE

(75) Inventors: Ariel Ben-Porath, Gealia (IL); Douglas Ray Hendricks, San Jose, CA (US)

(73) Assignee: Applied Materials, Israel, Ltd., Rehovot (IL)

( * ) Notice: Subject to any disclaimer, the term of this patent is extended or adjusted under 35 U.S.C. 154(b) by 72 days.

(21) Appl. No.: 10/327,537

(22) Filed: Dec. 19, 2002

(65) Prior Publication Data

US 2004/0121497 A1 Jun. 24, 2004

(51) Int. Cl.
*H01L 21/00* (2006.01)
*H01L 21/66* (2006.01)
*H01L 23/58* (2006.01)
*G01R 33/02* (2006.01)
*G01R 31/26* (2006.01)

(52) U.S. Cl. ............................ 438/11; 438/14; 438/117; 257/48; 324/252; 324/719; 324/765

(58) Field of Classification Search ................... 438/14, 438/17
See application file for complete search history.

(56) References Cited

U.S. PATENT DOCUMENTS 4,292,519 A * 9/1981 Feuerbaum ................. 250/310
5,929,643 A * 7/1999 Sakai et al. ................. 324/750

(Continued)

FOREIGN PATENT DOCUMENTS

JP 358154244 * 9/1983

(Continued)

OTHER PUBLICATIONS

PCT International Search Report for Application No. PCT/US 03/40919, dated Oct. 5, 2004, 6 pages.

Primary Examiner—Carl Whitehead, Jr.
Assistant Examiner—James M. Mitchell
(74) Attorney, Agent, or Firm—Tarek N. Fahmi (57) ABSTRACT

A method for electrically testing a semiconductor wafer during integrated-circuit fabrication process, the method including: (i) providing a scanning charged-particle microscope (SCPM), having a defined scanning plane and operative, while in any one mechanical state, to scan a surface in the scanning plane within a two-dimensional scanning window, which has a given maximum size; (ii) providing in association with any layer of the wafer, it being a test layer, one or more test structures, each test structure including normally conductive areas within a normally non-conductive background in one or more layers, which include said test layer, the conductive areas formed as one or more patterns; the patterns in said test layer include one or more clusters of mutually isolated pads; each pad is conductively connected with a corresponding distinct point on the patterns and all the pads in any one cluster are sized and arranged so that at least a significant portion of each pad falls within a common window whose size does not exceed said maximum size of said scanning window; (iii) with said test layer forming the top surface of the wafer, placing the wafer on the SCPM and adjusting the mechanical state of the SCPM so that at least a significant portion of each pad in any one of said clusters is within said scanning window; (iv) causing the SCPM, while in said mechanical state, to scan all of the pads of said one cluster and thereby to provide information about the electrical state of the respective test structure.

20 Claims, 6 Drawing Sheets

U.S. PATENT DOCUMENTS

| | | | |
|---|---|---|---|
| 5,940,678 A * | 8/1999 | Doong et al. | 438/14 |
| 5,959,459 A | 9/1999 | Satya et al. | |
| 6,091,249 A * | 7/2000 | Talbot et al. | 324/751 |
| 6,204,075 B1 * | 3/2001 | Kikuchi | 438/18 |
| 6,297,644 B1 * | 10/2001 | Jarvis et al. | 324/537 |
| 6,329,826 B1 * | 12/2001 | Shinada et al. | 324/751 |
| 6,448,099 B1 * | 9/2002 | Iacoponi et al. | 438/17 |
| 6,452,412 B1 | 9/2002 | Jarvis et al. | |
| 6,504,393 B1 * | 1/2003 | Lo et al. | 324/765 |
| 6,516,450 B1 * | 2/2003 | Hill et al. | 716/4 |
| 6,809,534 B2 * | 10/2004 | Yamada | 324/751 |
| 6,853,204 B2 * | 2/2005 | Nishiyama et al. | 324/751 |
| 7,015,418 B2 * | 3/2006 | Cahill et al. | 219/121.69 |
| 2002/0085761 A1 * | 7/2002 | Cao et al. | 382/209 |
| 2002/0093350 A1 * | 7/2002 | Yamada | 324/751 |
| 2002/0113598 A1 * | 8/2002 | Tsuji et al. | 324/501 |
| 2002/0125905 A1 * | 9/2002 | Borden et al. | 324/765 |
| 2002/0187582 A1 * | 12/2002 | Satya et al. | 438/48 |
| 2004/0084671 A1 * | 5/2004 | Song et al. | 257/48 |

FOREIGN PATENT DOCUMENTS

| | | | | |
|---|---|---|---|---|
| JP | 4-18399 | * | 1/1992 | 283/72 |
| WO | WO 01/80304 A2 | | 10/2001 | |

* cited by examiner

VOLTAGE CONTRAST TEST STRUCTURE

FIELD OF THE INVENTION

This invention relates to inspecting and testing semiconductors wafers during circuit fabrication and, in particular, to test structures for electrical testing with an electron beam in voltage-contrast mode.

BACKGROUND OF THE INVENTION

Routine inspection of the surface of semiconductor wafers during the fabrication of integrated circuits thereon is commonly carried out by a combination of optical inspection of the entire surface and high-resolution electron beam inspection of suspected spots. Characterization of apparent defects detected during such inspection operation must be correlated with actual faults in the fabricated circuits. Such a correlation is obtained, with respect to any particular fabrication process, by the inclusion of suitable electrical test structures in one or more layers of the wafer. The test structures undergo the same processing as the other circuits and are inspected by the aforementioned means. In addition, however, they are also tested electrically, so as to detect any electrical faults, namely "opens" and "shorts". The results of the electrical tests are compared with the observations from the inspection operations—to establish correlation. This procedure must be performed at least once whenever a new fabrication process is introduced or even when a process is modified; to this end, an array of test patterns that fills the entire area of a special wafer may be used. Additionally, however, the procedure must be repeated periodically, preferably even for every wafer being fabricated, in order to continuously follow, and possibly monitor, any changes that occur in the fabrication process. To this end, test structures are interspersed between the regular chip patterns—preferably within the scribe-lines.

According to prior art, the electrical testing is done by means of probes that are made to contact suitable conductive pads in the test structures. This method has two major drawbacks: (a) To assure mechanical alignment between the probes and the pads, the latter must be made relatively large, thus taking valuable "real estate" from the wafer. (b) The wafer must be placed in the contact-testing device, which is separate from the inspection device, thus incurring extra time and labor. These drawbacks are particularly significant for routine monitoring operation.

More recently, electrical testing by means of an electron beam has come into practice, as disclosed for example in U.S. Pat. No. 5,959,459 and European Patent WO 01/80304. In this method, an electron-beam device, such as a scanning electron microscope (SEM) used for high-resolution wafer inspection, is made to first deposit electrical charges at certain points of a test pattern (usually provided with suitable pads), which charges either remain in the respective circuit elements or are dissipated to ground. The electron-beam device is then made to scan the pattern in a so-called voltage contrast mode, whereby electrons are variously emitted from the surface according to the voltages thereon and collected, to form a sensing current. The latter is then processed to form a so-called voltage-contrast image, which is subsequently interpreted to indicate shorts and opens in the corresponding circuit elements. This method largely overcomes the drawbacks of the contact testing method, enumerated above, in that the pads may be made appreciably smaller and in that the same electron-beam device (namely a SEM) may be used for both electrical testing and inspection for defects.

In prior-art systems that utilize electron beam devices for electrical testing of test structures, scanning of a particular pattern, during both the charging phase and the sensing phase, extends essentially over the entire width of the pattern along one of the two coordinate axes; scanning along the other axis, which necessarily involves mechanical motion, is inherently slow. Moreover, in order to make it reasonably fast, the scanning path is usually linear; this constrains the design of the test structure, and in particular impedes compactness.

Thus there is a clear need for a compact class of test structures and for a method for fast electrical testing of such structures on wafers, utilizing scanning charged-particle beam devices, such as a scanning electron-beam microscope.

SUMMARY OF THE INVENTION

The present invention is of a class of test structures, to be included in any one or more conductive (e.g. metal or polysilicon) layers of an integrated circuits wafer, that are electrically testable by means of a particular class of charged-particle-beam devices. This class of devices is characterized by the ability to deflect the beam along both coordinate axes; normally such deflection is made in the pattern of a raster of essentially parallel lines, covering an essentially rectangular scan window. Typical for this class of devices, but not limiting, is a scanning electron-beam microscope (SEM), "SEMVision", made by Applied Materials Corp. of Santa Clara, Calif., which mainly serves for high-resolution inspection of the surface of a wafer between fabrication stages for the detection and characterization of fabrication defects. In common with other charged-particle-beam devices, devices of this class are capable of operation in a charging mode and in a voltage contrast sensing mode, as explained above in the Background section. These devices, in common, are also designed so that the target object, e.g. the wafer, can be moved so that any portion of its surface be placed under the scanning beam. However, in the particular class aimed at by the invention, the object is typically at rest during any one scanning operation. For brevity, a charged-particle-beam device addressed by the invention will be referred to hereunder as a SEM, and, moreover, all the embodiments will be described as utilizing a SEM, but this should not be construed as limiting the invention.

The test structures of the invention are characterized by each having any number of conductive segments, in various geometric patterns and variously interconnected, and a number of conductive pads that are clustered together in one or more clusters so as to be scannable by the SEM while holding the wafer stationary; each pad is conductively connected to a corresponding point on some one of the conductive segments. A cluster is characterized by having the pads in close proximity to each other and so that all, or a significant portion of them, are within a window representing the maximum scan raster of the SEM. Any particular structure is designed so that voltages sensed on the various pads are indicative of electrical faults—mainly shorts and/or discontinuities (opens)—within the structure. For example, a particular structure may be designed to test discontinuities in circuit lines within any one layer, another—to test shorts between lines and yet another—to test discontinuities in interlayer connections (vias). The faults may be traceable to a particular region of the structure, associated with the cluster being scanned and defined by the extent of the patterns connected to pads in the cluster; alternatively, the faults may be traceable to particular sections within the region, associated (by virtue of connection) with individual pads in the cluster. The presence or absence of faults in a test structure and the location of any such faults will be referred to generally as the electrical state of the structure. It is noted that the size of any region, i.e. the extent of any patterns of conductive segments connected to pads in the associated cluster, is substantially larger than the size of the cluster and, per force, is substantially larger than the maximum size of a scanning window of the SEM.

As with any previous electrical testing method, several copies, or instances, of one or more particular test structures according to the invention are usually placed in any appropriate layer of the wafer. Some or all of these structures may be appropriately shaped and placed within the scribe-line areas. After the fabrication stage of that layer, the wafer is placed in the SEM. The latter is programmed to sequentially test each instance of the structure by placing the respective cluster of pads under the beam, then, without moving the wafer, scan it in a charging mode, followed by scanning in a voltage-contrast sensing mode; all scanning is preferably in a rectangular raster pattern. Optionally, after obtaining results of the testing and while the wafer is still held in the SEM, it may be moved sequentially so as to position each region in which a fault has thus been detected under the beam and to scan it in the normal inspection mode; the observed image may then be correlated with the corresponding type of electrical fault.

Advantages of test structures according to the invention are:
(a) higher speed, since the scanning action is purely electronic and since essentially no time is wasted scanning structure portions other than the pads;
(b) no limit on the size of a structure, as would otherwise be imposed by the span of the scanning pattern;
(c) relative compactness and freedom of design for a given complexity of pattern, since the pads are outside the pattern.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1A:
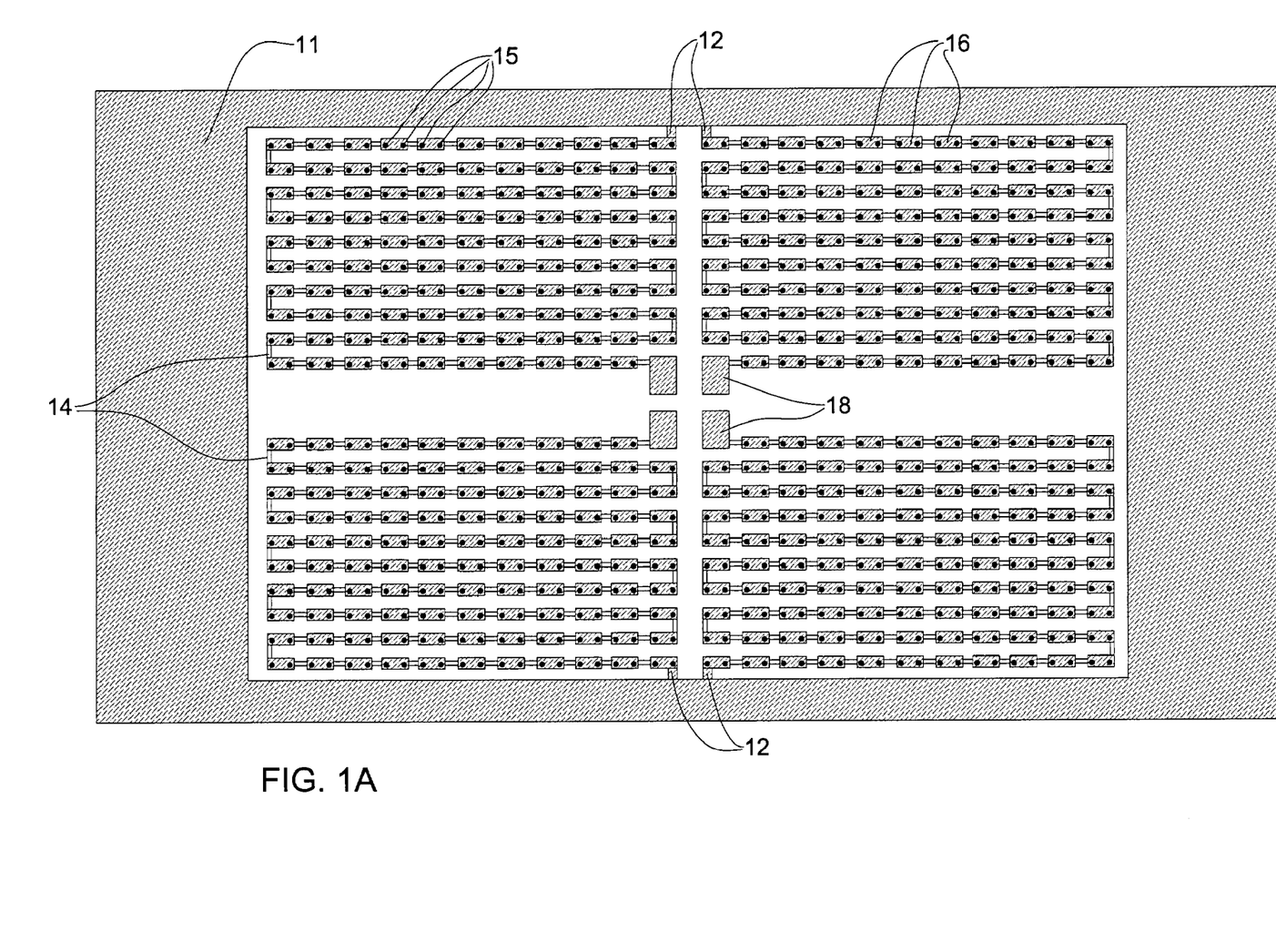
FIGS. 1A–1D are typical patterns of various test structures according to the invention.

FIG. 1A shows, by way of example, a pattern of a particular test structure according to the invention, designed to test for discontinuities, i.e. faulty open-circuit conditions, in interlayer connections (vias). The pattern is sized, along one dimension, to fit within a scribe-line; the size along the other dimension may be any. The structure consists of four conductive circuits 14, symmetrically arranged in respective quadrants of the rectangular pattern. Each circuit consists of a large number of conducting segments 16 on each of two layers, only the upper one of which is shown; the segments on the lower layer are schematically represented in the drawing by short lines appearing to connect between the upper segments. The segments are connected in series, alternatingly between the layers, through vias 15, to form a single conductive chain. One end of each chain (i.e. circuit) is connected to a virtual ground 11, at points 12, and the other end is connected to a pad 18 near the center of the pattern. The four pads 18 are arranged as a cluster, preferably in a symmetrical manner about the center of the pattern. Virtual ground 11 is usually a relatively large conductive area, preferably in the test layer, which, owing to strong capacitive coupling to other layers, maintains an essentially constant voltage near ground level.

It is noted that the entire rectangular area that contains the patterns of the four circuits constitutes a region that is associated with the cluster of pads at the center. It is further noted that each quadrant, containing the pattern of a respective circuit, constitutes a section of the region that is associated with the respective pad. If the exemplary test structure of FIG. 1A included additional clusters of pads, each connected to additional circuits, the patterns of the latter would define corresponding additional regions and sections, associated with the respective additional clusters and pads.

The patterns in the four quadrants in FIG. 1A are shown to be identical; however in practice they may be different. They could consist of entirely different circuits or of identically patterned circuits but with slightly different features or dimensional parameters. In the latter case, they would be subject to faults under slightly different fabrication process conditions, or may have different probabilities of faults under given conditions—all of which may be utilized for sensitive monitoring of the process. It will be appreciated that the number of circuits in the structure, and consequently the number of pads, may also be different from four—for example, two, six or eight.

It is noted that in the present example, the test structure consists of conductive patterns in each of two layers, to be fabricated in corresponding two layers on the wafer, and of vias to be fabricated in the intervening layer (or layers). However, only the pattern in the top one of these layers includes pads; this is the rule for all multi-layered test structures and it is this top layer that is formally associated with any such structure and should be understood as the layer that carries the structure; this layer will also be referred to, with respect to any test structure that it carries, as the test layer. Clearly, in the case of a single-layer test structure (such as are exemplified in FIGS. 1C and 1D, to be described below), it is that single layer that serves as the test layer and is associated with the structure.

Figure 2A:
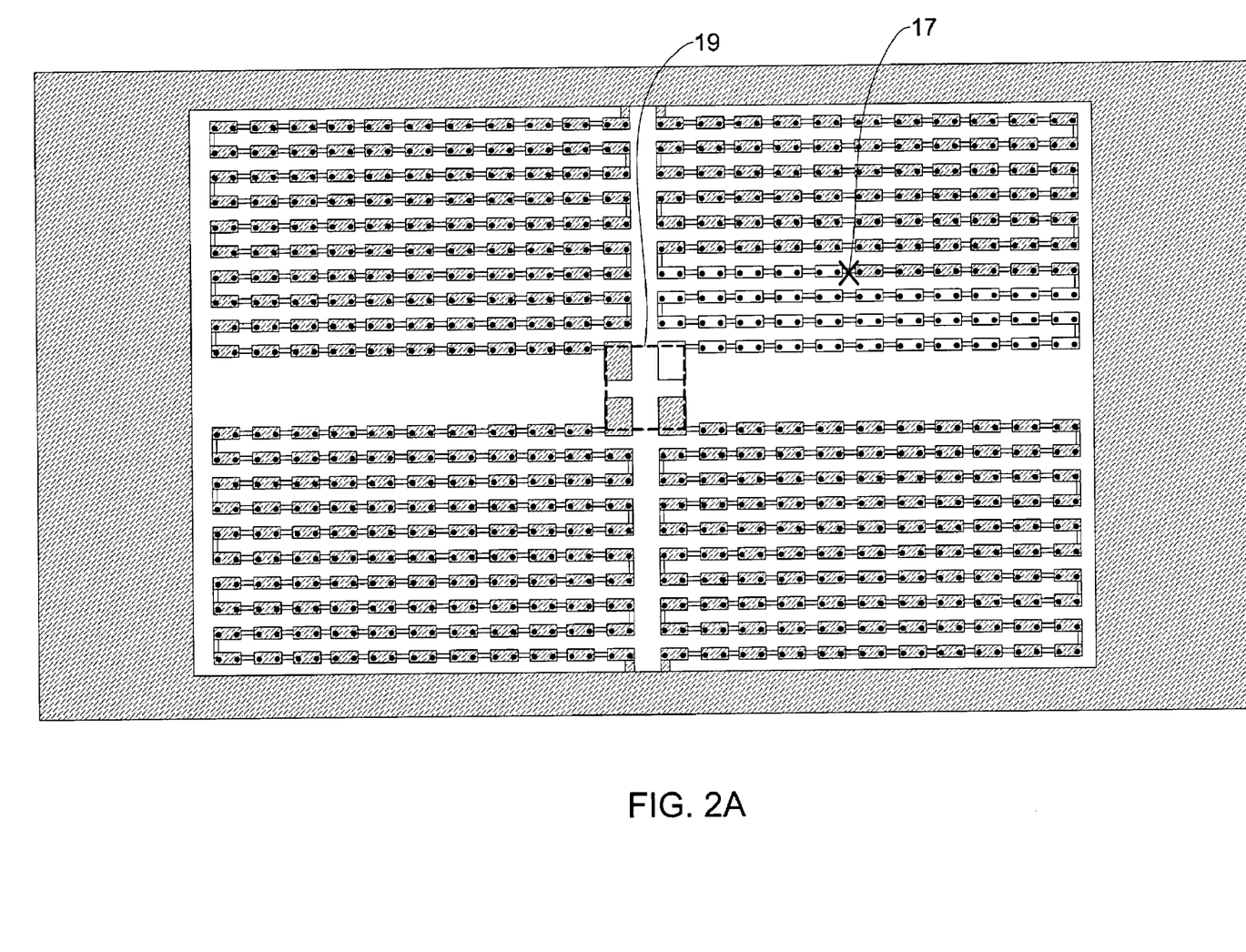
FIG. 2A schematically depicts the sensing conditions on the structure of FIG. 1a under an assumed fault.

During test operation, a wafer, carrying instances of the structure in its currently top layer, i.e. the layer that has just been fabricated (and referred to as a test layer), is placed in a SEM and, for each instance, the following procedure is carried out automatically, under control of a suitable program; the procedure is illustrated with reference to FIG. 2A, which shows a test pattern identical to that of FIG. 1A:

(a) The wafer is positioned so that the cluster of pads is symmetrically concentric with the scanning window, represented here by a dashed rectangle 19; it is noted that the window need not include the entire area of the pads, but it preferably includes an equal area of each pad, the area being also preferably a significant portion of each pad.

(b) The SEM is operated in a charging mode, while raster-scanning the window area, long enough to charge up any ungrounded circuit to a significant voltage level.

(c) While the wafer remains in the same stationary position and still raster-scanning the window area, the SEM is operated in a voltage-contrast mode, until a voltage-contrast image is obtained.

(d) The obtained image is interpreted so as to indicate faults. In the exemplary situation of FIG. 2a, three pads show a ground-level voltage (represented here by a dark color), indicating normal continuity to ground, while the pad of the upper-right quadrant shows a significant voltage level (represented here by a light color), indicating a discontinuity (an open circuit) in that quadrant. For the sake of didactic demonstration, all the segments of the circuit between the pad and the open via, marked by an X 17, are here marked as being at a high voltage level (indicated by the light color); in practice, however, only the voltages at the pads are being sensed. Optionally, the wafer could be moved so as to place any other portion of the circuit under the scanning window and then scanned in a voltage-contrast mode; thus the location of the fault may be more narrowly determined, especially by repeating such moving and scanning cycle.

Figure 1B:
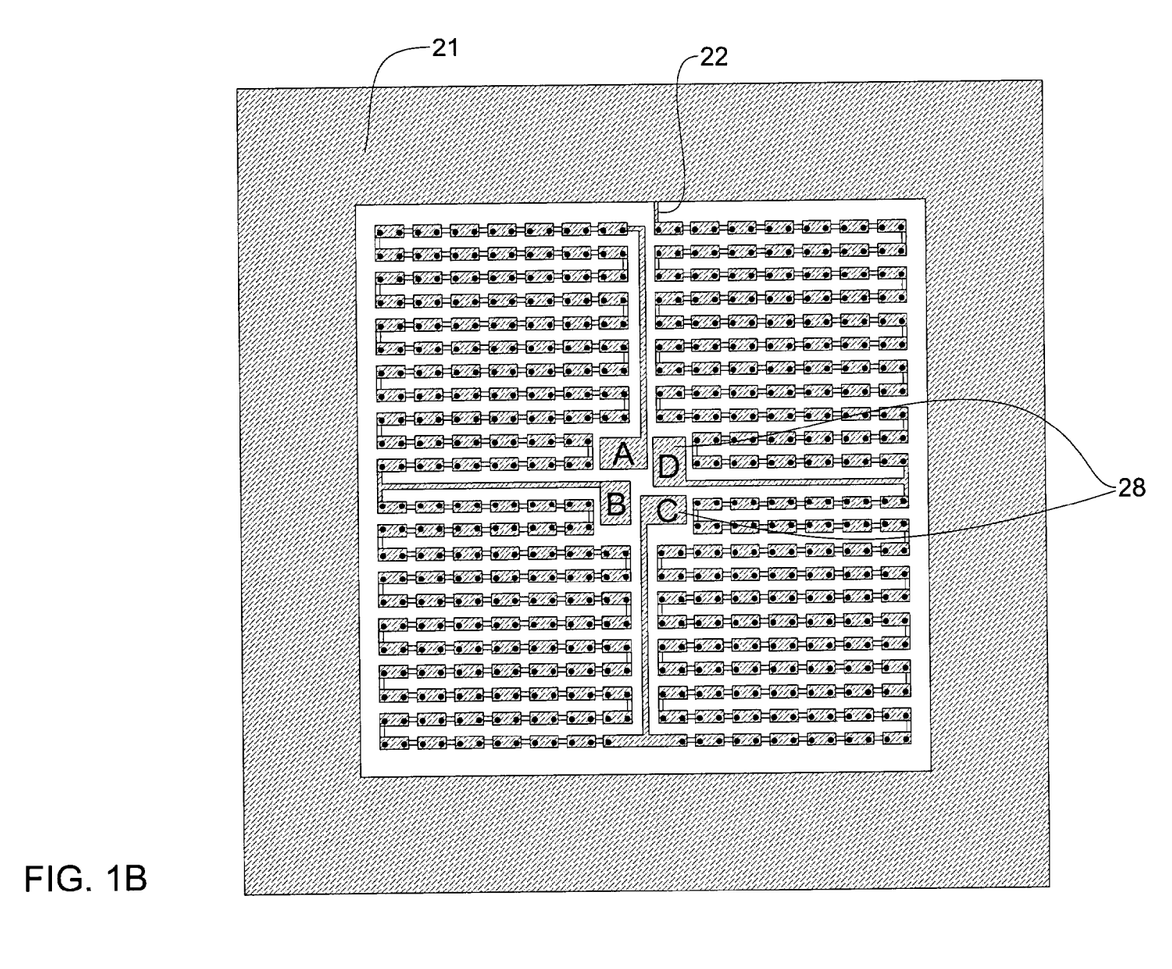

FIG. 1B shows the pattern of another exemplary test structure according to the invention. It is similar to that of FIG. 1A in that it also is designed to test for discontinuities in vias, which electrically connect alternating conductive segments in two respective layers, and in that it is patterned in four quadrants and has a central cluster of four pads. However, in this case, the pattern happens not to be sized to a scribe-line and, more significantly, the structure consists of a single circuit, that is—of a single chain of segments, interconnected by vias and connected at one end 22 to a virtual ground plane 21. The other end of the chain and three intermediate points are connected each to one of the four pads 28—marked A, B, C and D, respectively. The three intermediate points are located so that they divide the circuit into four sections, which are arranged in respective quadrants of the pattern. It is noted that the four sections may also be regarded as four circuits that are connected in series. It will be appreciated that other schemes of dividing the pattern into sections and forming them into regions may likewise be employed and that the number of connection points and the corresponding number of pads may be higher or lower than in FIG. 1B.

Figure 2B:
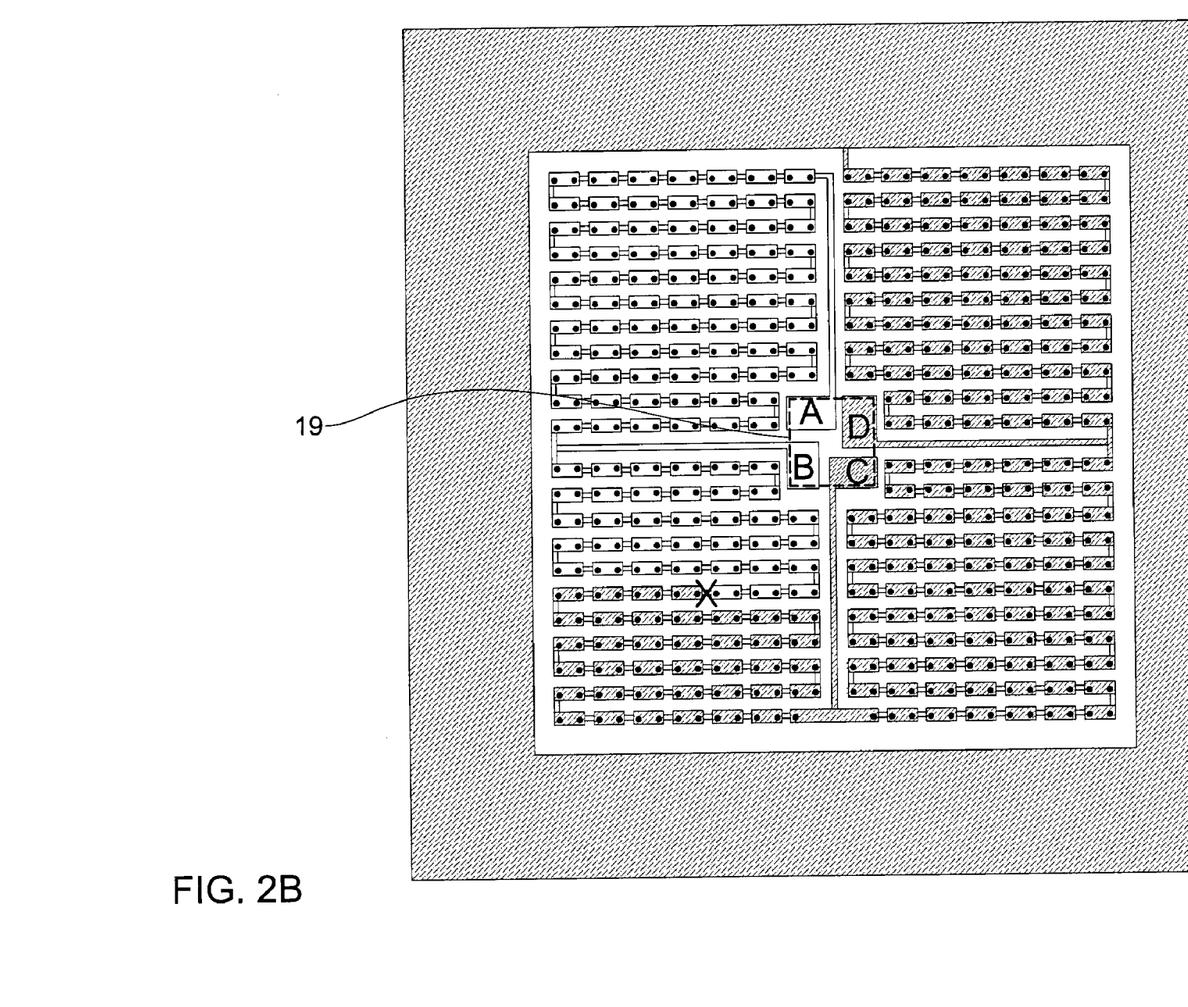
FIG. 2B schematically depicts the sensing conditions on the structure of FIG. 1b under an assumed fault condition.

During test operation, a wafer, carrying instances of the structure at the currently top layer, is again placed in a SEM and, for each instance, the following procedure, with reference to FIG. 2B, is carried out automatically, under control of a suitable program:

(a) The wafer is positioned so that pad A is concentric with the scanning window, which, in turn, is adjusted to fall entirely within the pad area.

(b) The SEM is operated in a charging mode, while raster-scanning the window area, long enough to charge up any ungrounded circuit to a significant voltage level.

(c) The wafer is repositioned so that the whole cluster of pads is symmetrically concentric with the scanning window 19, which, in turn, is adjusted to cover most of the cluster area (though it need not include the entirety of each pad) and the SEM is operated in a voltage-contrast mode, while raster-scanning the window area, until a voltage-contrast image of the pads is obtained.

Figure 3:
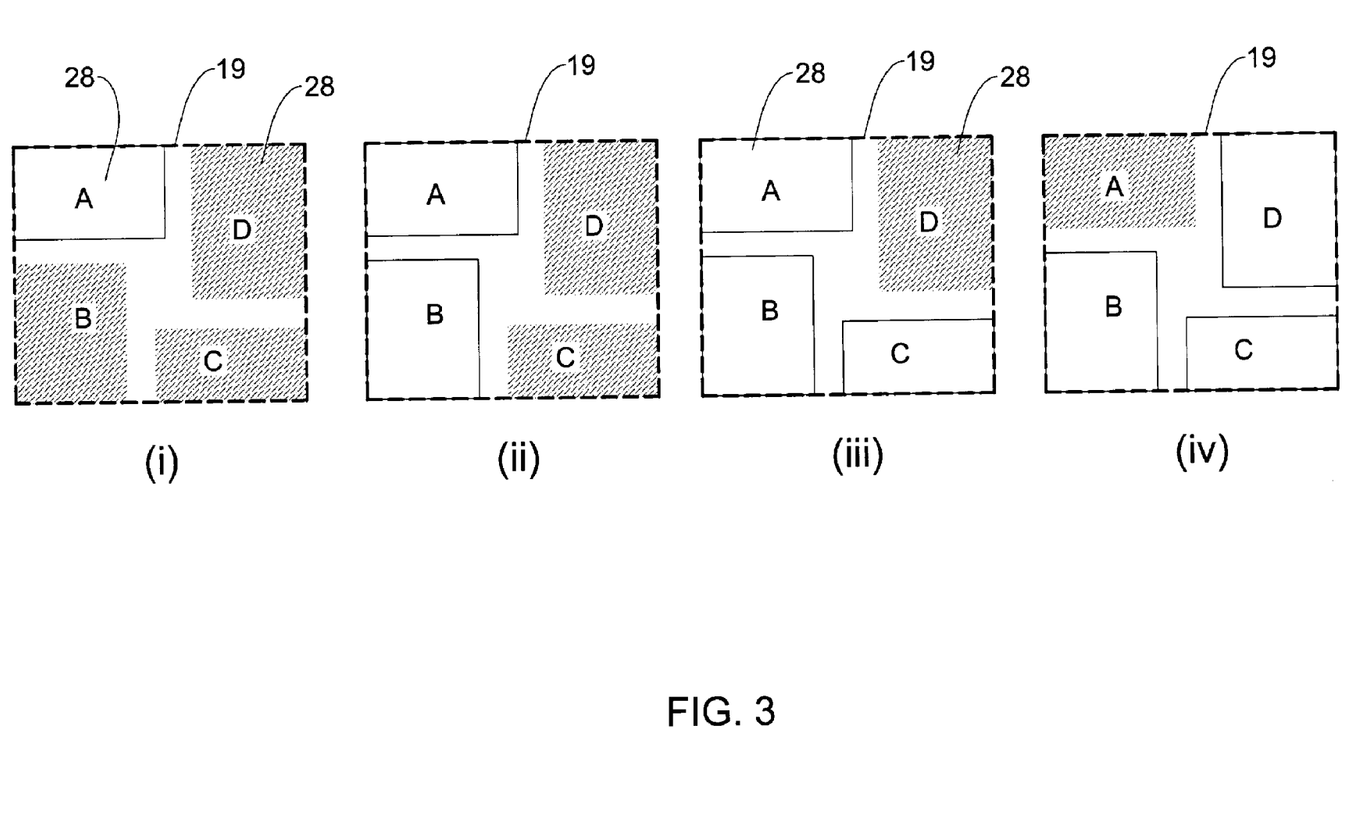
FIG. 3 schematically depicts the sensing conditions in the pads of the structure of FIG. 1b under various assumed fault conditions.

(d) The obtained image is interpreted so as to indicate faults. In FIG. 3 four exemplary situations are illustrated, represented receptively by four images of the scanning window, marked (i)–(iv); the situation illustrated by image (ii) is also depicted in FIG. 2B, in the same manner as in FIG. 1B, discussed above. In each case, dark areas signify ground-level voltage, indicating normal continuity to ground, while light areas signify some non-zero voltage, indicating an open circuit condition. In the situation depicted in FIG. 3 by image (i), only pad A is at ground level—indicating a discontinuity in the upper-left quadrant. In image (ii), as in FIG. 2B, both pads A and B are low—indicating a discontinuity in the lower-left quadrant. It is observed that the discontinuity occurs in this case at the point marked X; however, the location of X within the circuit (i.e. within the quadrant) is not directly discernible from this measurement. Similarly, pads A, B and C being low in image (iii) indicate an open circuit in the lower-right quadrant and all four pads being low, as in image (iv), indicate an open circuit in the upper-right quadrant.

Figure 1C:
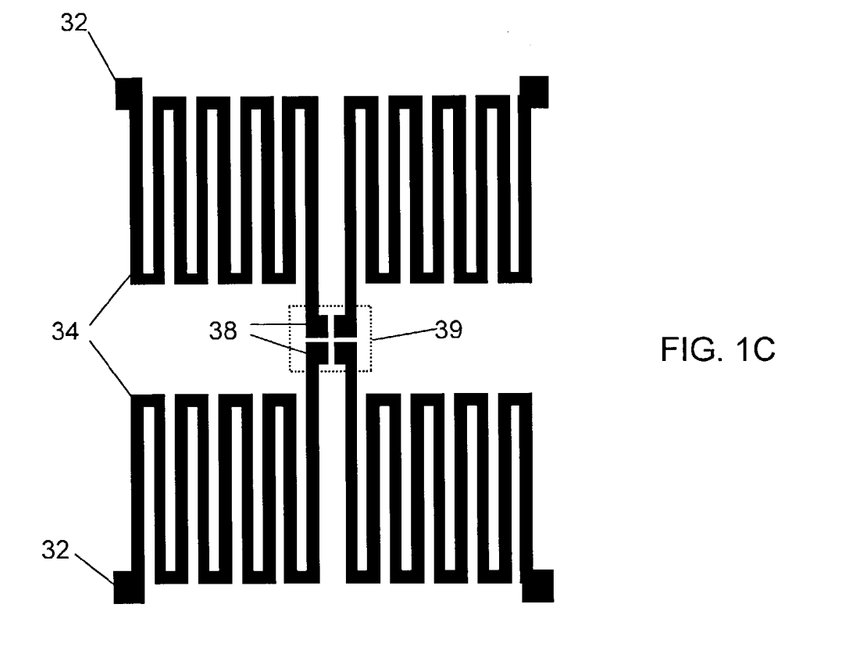

FIG. 1C shows schematically yet another exemplary test structure according to the invention. It is designed to test for faulty discontinuities in long conducting lines of minimal width within a single layer. The structure consists, again, of four separate circuits 34, in respective quadrants, each circuit having a serpentine pattern, thus being largely similar to that of FIG. 1A, except that it is a continuous line (i.e. does not include vias). Each circuit 34 has a pad 38 at one end, while the other end 32 is connected to a virtual-ground (not shown). Its manner of usage during testing is similar to that described above with respect to FIG. 1A and with reference to FIG. 2A, namely scanning the four pads within a stationary scanning window 39. It is noted that the pattern of FIG. 1B and its manner of usage could equally be adapted to the case of a continuous conductor.

Figure 1D:
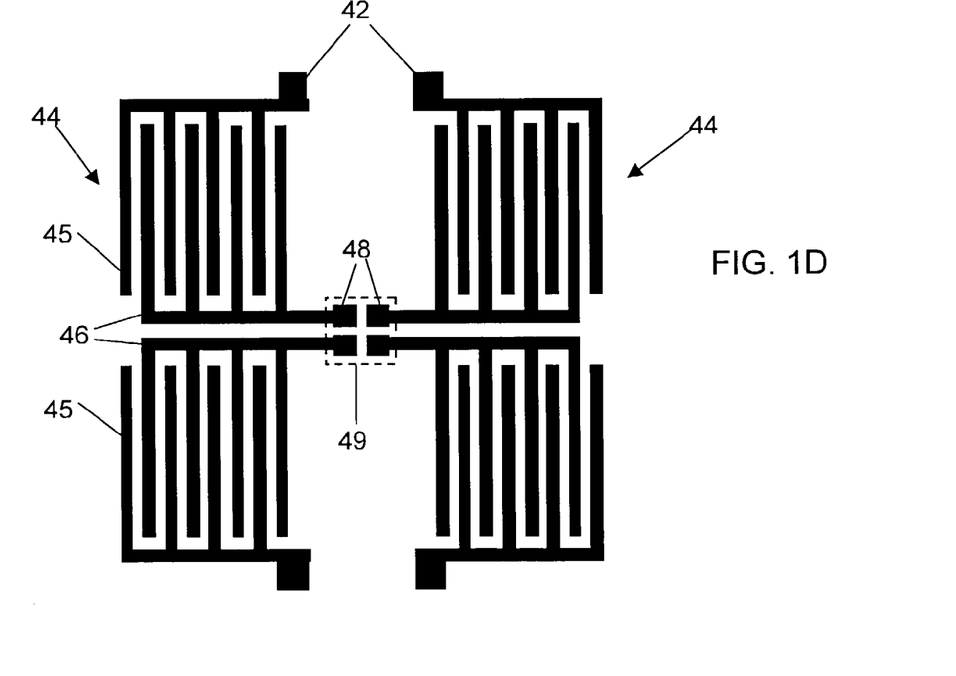

FIG. 1D shows schematically still another exemplary test structure according to the invention. It is designed to test for faulty short-circuit conditions between long conducting lines at minimal spacing between them within a single layer. It is seen to include four identical isolation patterns 44, one in each quadrant, each isolation pattern consisting of a pair of mutually isolated conductors, each shaped like a comb with a plurality of parallel "teeth", the teeth of the two conductors in a pair being intertwined at close proximity. One member 45 of each pair is connected, at point 42, to a virtual ground plane (not shown), while the other member 46 is connected to a corresponding pad 48. The pads 48 form a cluster at the center of the structure. Test operation with this structure is largely similar to that with the structure of FIG. 1A, as illustrated by FIG. 2A, including scanning the four pads within a stationary scanning window 49; the main difference is in the manner of interpreting the resultant voltage contrast image of the pads, namely: Ground-level voltage in any pad indicates a short between the respective pair of conductors, while any significant voltage level in a pad indicates normal (i.e. isolation) condition in the respective pair. It is noted that in the exemplary structure of FIG. 1D the entire patterned rectangle forms a region, associated with the cluster at the center, and each pair of mutually proximate conductors forms a section, associated with a respective pad. It is also noted that, since in this case one conductor of each isolation pattern is connected to a common conductive area, which constitutes virtual ground, all such conductors in the region may be regarded as a single conductor.

It will be appreciated that, even though all the exemplary structures discussed above have a cluster of four pads at their centers, any other number of pads can be used and the cluster of pads may also be placed at any other point within its region, or at its edge or even outside the area defined by the circuits pattern. Moreover, several test structures could be placed in general proximity to each other and their pads, being generally external to each structure, could all be clustered together. In usage they would then be scanned together, in one or both modes of SEM operation, in a manner similar to that described above with respect to FIG. 2A or FIG. 2B. Another possibility is for any one test structure to include a plurality of pad clusters; that is—pads connected to various points in the structure are formed into a plurality of clusters, the clusters variously positioned within or without the area defined by the patterns of the structure and each associated with a corresponding region within the overall pattern.

It will also be appreciated that many more different structures and patterns are possible, all coming within the scope of the invention, as defined in the claims to follow.

The invention claimed is:

1. A method for electrically testing a semiconductor wafer during integrated-circuit fabrication process, the method comprising:

scanning a zone on a surface of the semiconductor wafer, while the semiconductor wafer is kept stationary, with a scanning charged-particle microscope (SCPM) having a scanning window, which has a given maximum size;

the surface having one or more test structures including one or more patterns comprised of interconnected conducting segments conductively coupled to one or more clusters of mutually isolated pads where each pad is conductively connected with a corresponding distinct point on the one or more patterns and all the pads in any one cluster are sized and arranged so that at least a significant portion of each pad falls within the zone; wherein the zone is sized such that it does not exceed the given maximum size of the scanning window of the SCPM; and obtaining information about the electrical state of the one or more test structures associated with each pad.

2. The method of claim 1, wherein each of the one or more clusters is associated with a corresponding region within a respective test structure and the information about the electrical state is indicative of faults in the corresponding region.

3. The method of claim 2, wherein any region is substantially larger than the given maximum size of the scanning window.

4. The method of claim 2, wherein any region includes at least one conductive circuit, a first end of which is connected to a corresponding pad in the associated cluster and a second end of which is connected to a point characterized by an essentially constant voltage level.

5. The method of claim 4, wherein, with respect to any of the at least one conductive circuit, no other point in the circuit is connected to a pad and the information about the electrical state is indicative of a discontinuity in the circuit.

6. The method of claim 4, wherein, with respect to any of the at least one conductive circuit, one or more intermediate points on the circuit are connected each to a corresponding pad in the associated cluster.

7. The method of claim 6, wherein the circuit is divided by the intermediate points into sections and the information about the electrical state is indicative of a discontinuity in the circuit and of a section in which the discontinuity is located.

8. The method of claim 4, wherein the circuit is formed in a serpentine pattern.

9. The method of claim 4, wherein the circuit is formed as a plurality of conductive segments on each of a plurality of layers, interconnected by vias.

10. The method of claim 2, wherein any region includes at least one isolation pattern, each consisting of two or more mutually isolated conductors, a first one of the conductors being connected to a point characterized by a predetermnined voltage level and the other conductors being in close proximity to the first conductor and connected each to a respective pad in the associated cluster.

11. The method of claim 10, wherein each of the conductors is formed as a comb with teeth, the teeth of the first conductor in any isolation pattern meshing with the teeth of any of the corresponding other conductors.

12. The method of claim 10, wherein, with respect to any of said other conductors, the information obtained about the electrical state is indicative of a short between the conductor and said first conductor in the respective isolation pattern.

13. The method of claim 2, further comprising:

causing the SCPM to scan any region, or any section thereof in which a fault has been found.

14. The method of claim 1, wherein scanning includes scanning successively in two special modes, the first special mode causing a given electrical charge to be deposited on each pad in the zone and the second special mode, subsequent to the first special mode, being a voltage contrast mode.

15. The method of claim 14, wherein results of scanning in voltage contrast mode are compared with corresponding given normal values and any significant difference between the results and the given normal values is indicative of a fault in a respective test structure.

16. The method of claim 15, further comprising:

causing the SCPM to scan, in normal mode, any test structure in which a fault indication has been found.

17. The method of claim 1, wherein the SCPM is a scanning electron microscope.

18. The method of claim 1, further comprising:

causing the SCPM to scan any area of any of the test structures, the scanned area being determined based on the information about the electrical state.

19. The method of claim 1, wherein each test structure has a size substantially larger than the given maximum size of the scanning window.

20. The method of claim 1, wherein any test structure includes a conductive area which is a substantial portion of the test structure and which serves, during testing, to hold an essentially constant voltage level.

* * * * *